United States Patent
Carey et al.

(10) Patent No.: US 12,339,291 B2
(45) Date of Patent: Jun. 24, 2025

(54) LIPID-DNA LABELING OF LIPID BILAYER PARTICLES FOR AMPLIFICATION QUANTITATION

(71) Applicant: The Regents of the University of California, Oakland, CA (US)

(72) Inventors: Thomas Robert Carey, Berkeley, CA (US); Molly Aliza Kozminsky, Berkeley, CA (US); Lydia L. Sohn, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 684 days.

(21) Appl. No.: 17/749,163

(22) Filed: May 20, 2022

(65) Prior Publication Data
US 2022/0276266 A1 Sep. 1, 2022

Related U.S. Application Data (63) Continuation of application No. PCT/US2020/062957, filed on Dec. 2, 2020.

(60) Provisional application No. 62/942,216, filed on Dec. 2, 2019.

(51) Int. Cl.
*G01N 33/92* (2006.01)
*C12Q 1/6851* (2018.01)

(52) U.S. Cl.
CPC .......... *G01N 33/92* (2013.01); *C12Q 1/6851* (2013.01); *G01N 2458/10* (2013.01)

(58) Field of Classification Search
None
See application file for complete search history.

(56) References Cited

PUBLICATIONS

Weber et al. Efficient Targeting of Fatty-Acid Modified Oligonucleotides to Live Cell Membranes through Stepwise Assembly. Biomacromolecules. Dec. 8, 2014;15(12):4621-6.*

* cited by examiner

*Primary Examiner* — Nianxiang Zou
(74) *Attorney, Agent, or Firm* — Richard Aron Osman (57) ABSTRACT

Lipid bilayer particles, such as extracellular vesicles (EVs), are labeled with lipid-tagged single-stranded DNA (ssDNA), which is amplified by polymerase chain reaction (PCR) to quantify particles captured via surface marker interactions or complementary oligonucleotide hybridization.

20 Claims, 7 Drawing Sheets

LIPID-DNA LABELING OF LIPID BILAYER PARTICLES FOR AMPLIFICATION QUANTITATION

This invention was made with government support under Grant Numbers CA190843 awarded by the National Institutes of Health. The government has certain rights in the invention.

INTRODUCTION

We disclose a method to quantify the number of lipid bilayer particles, such as extracellular vesicles (EVs), enveloped viruses, outer membrane vesicles, or liposomes, which may be isolated from human or animal bodily fluids, e.g. saliva, urine, blood, interstitial fluid), a cell culture medium, a medium containing bacteria, or synthesized, expressing/displaying specific surface antigens. Our method is orders of magnitude more sensitive than existing EV detection/characterization methods, permitting detection of single EVs. Currently, the most sensitive EV detection strategy is based on isolating EV subpopulations using immunocapture and then quantifying capture of EVs with a specific phenotype by amplifying endogenous RNA or DNA found within EVs [1, 2, 3]. A limitation of this current strategy is that any given RNA or DNA sequence is sparsely distributed, i.e. the ratio of number of copies of any RNA sequence to the number of EVs is <1 [4].

SUMMARY OF THE INVENTION

The invention leverages DNA oligo tagging for lipid bilayer particles (e.g. extracellular vesicles (EVs), enveloped viruses, or liposomes), wherein the particles are labeled with lipid-tagged single-stranded DNA (ssDNA), which can be used to pattern particles on a surface or be amplified by polymerase chain reaction (PCR) to quantify particles captured via specific antigen binding or complementary oligonucleotide hybridization.

Applications include disease diagnosis, monitoring and staging, personalized medicine, and drug discovery, such as sepsis detection, viral infection, traumatic brain injury/concussion detection, heart disease, cancer treatment response monitoring, particle characterization, and Alzheimer's/dementia detection and/or monitoring.

In an aspect the invention provides a method to quantify lipid bilayer particles expressing/displaying specific surface antigens, comprising:
  (a) labeling the particles with single-stranded DNAs (ssDNAs) each end-labeled with a membrane self-embedding lipid;
  (b) specifically capturing different subpopulations of the particles by specific antigen binding or complementary oligonucleotide sequence;
  (c) recovering intact particles by employing a restriction enzyme to release the ssDNA label after the capture;
  (d) using quantitative polymerase chain reaction (qPCR) quantification of the ssDNA to yield a quantitative readout that is directly correlated with the number of particles captured;
wherein the labeling step comprises combining the particles with:
  i. an anchor oligo comprising: lipid-anchor sequence-adhesion sequence;
  ii. a co-anchor oligo comprising: lipid-anchor sequence';
  iii. a detection oligo comprising: adhesion sequence'-detection sequence;

wherein the anchor oligo and at least one of the co-anchor oligo and detection oligo comprise complementary restriction sequences;
wherein the ' indicates reverse complement, and the anchor is in opposite orientation from the co-anchor and detection oligos, such that:
the lipids self-embed into the lipid bilayer membrane of the particles and anchor sequences hybridize via complementary base pairing, preventing the anchor oligo from dissociating from the membrane; the adhesion sequences hybridize, capturing the detection oligo onto the particles; and the restriction sequences hybridize, forming a double stranded restriction site.

In embodiments:
the anchor oligo and detection oligo comprise the complementary restriction sequences;
the anchor oligo and co-anchor oligo comprise the complementary restriction sequences;
the anchor oligo comprises: lipid-anchor sequence-adhesion sequence-restriction sequence; and the detection oligo comprises: adhesion sequence'-restriction sequence'-detection sequence;
the anchor oligo comprises: lipid-anchor sequence-restriction sequence-adhesion sequence; and the co-anchor oligo comprises: lipid-anchor sequence'-restriction sequence';
the anchor oligo comprises: 3'-5': lipid-anchor sequence-adhesion sequence; the co-anchor oligo comprises: 5'-3': lipid-anchor sequence'; and the detection oligo comprises: 5'-3': adhesion sequence'-detection sequence;
the anchor oligo comprises: 5'-3': lipid-anchor sequence-adhesion sequence; the co-anchor oligo comprises: 3'-5': lipid-anchor sequence'; and the detection oligo comprises: 3'-5': adhesion sequence'-detection sequence;
the anchor sequences are ≥10 nt, the adhesion sequences are ≥10 nt, the restriction sequences are 4-12 nt, and the detection sequence is ≥60 nt;
the anchor sequences are 10-1000, 10-300, 10-100 or 10-30 nt, the adhesion sequences are 10-1000, 10-300, 10-100 or 10-30 nt, the restriction sequences are 3-12, or 4-12 or 4-8 nt, and the detection sequence is 20-2000 or 20-500 or 20-100 nt;
the lipid is a steroid (such as cholesterol), lignoceric acid, dialkylphosphoglycerol, or a fatty acid amide see, e.g. Selden et al, J Am Chem Soc. 2012 Jan. 18; 134(2): 765-768; Weber et al. Biomacromolecules. 2014 Dec. 8; 15(12): 4621-4626;
the particles are isolated from a human or animal bodily fluid (e.g. saliva, urine, blood, interstitial fluid), a cell culture medium, a medium containing bacteria, or are synthesized;
the method quantifies a total number of particles and/or the quantities of different subpopulations of particles in a sample;
the capturing step comprises contacting the lipid bilayer particles with beads or surfaces functionalized with either a complementary oligonucleotide or a capture moiety (e.g. receptor protein, antibody, aptamer or nanobody) that binds specifically to the antigen, under conditions wherein particles displaying the antigen are retained on the beads or surfaces, and particles not displaying the antigen are washed away;
the method is in multiplex format, wherein the capturing step comprises contacting subsets of the particles in separate containers, each with beads or surfaces functionalized with a moiety to recognize a unique, specific antigen, under conditions wherein particles displaying the antigen are retained on the beads or surfaces, and particles not displaying the antigen are washed away; and/or the lipid bilayer particles are extracellular vesicles (EVs), enveloped viruses, outer membrane vesicles, or liposomes.

In an aspect the invention provides corresponding compositions and kits configured for practicing the methods, including an in vitro mixture comprising lipid bilayer particles, such as extracellular vesicles (EVs), and oligos:

i. an anchor oligo comprising: lipid-anchor sequence-adhesion sequence;
ii. a co-anchor oligo comprising: lipid-anchor sequence';
iii. a detection oligo comprising: adhesion sequence'-detection sequence;
wherein the anchor oligo and at least one of the co-anchor oligo and detection oligo comprise complementary restriction sequences;
wherein the ' indicates reverse complement, and the anchor is in opposite orientation from the co-anchor and detection oligos, such that:
the lipids self-embed into the lipid bilayer membrane of the particles and anchor sequences hybridize via complementary base pairing, preventing the anchor oligo from dissociating from the membrane; the adhesion sequences hybridize, capturing the detection oligo onto the particles; and the restriction sequences hybridize, forming a double stranded restriction site.

The invention encompasses all combinations of the particular embodiments recited herein, as if each combination had been laboriously recited.

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or. The examples and embodiments described herein are for illustrative purposes only and various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

We label each lipid bilayer particle with copies of synthetic lipid-tagged single-stranded DNA (ssDNA), then specifically capture particle subpopulations with moieties that bind specific antigens or oligonucleotide complementary to the ssDNA. qPCR quantification of this synthetic ssDNA yields a quantitative readout that is directly correlated with the number of particles captured. Our method further enables recovery of intact particles by employing a restriction enzyme to release the DNA label after capture. Our method provides rapid, nondestructive, and ultra-sensitive phenotyping of lipid bilayer particles and makes possible single-omics, multi-omics, and/or RNA-seq studies and subsequent systems biology and bioinformatics analysis from the same sample, such as proteomics, genomics, metabolomics, etc.

Figures 1A, 1B:
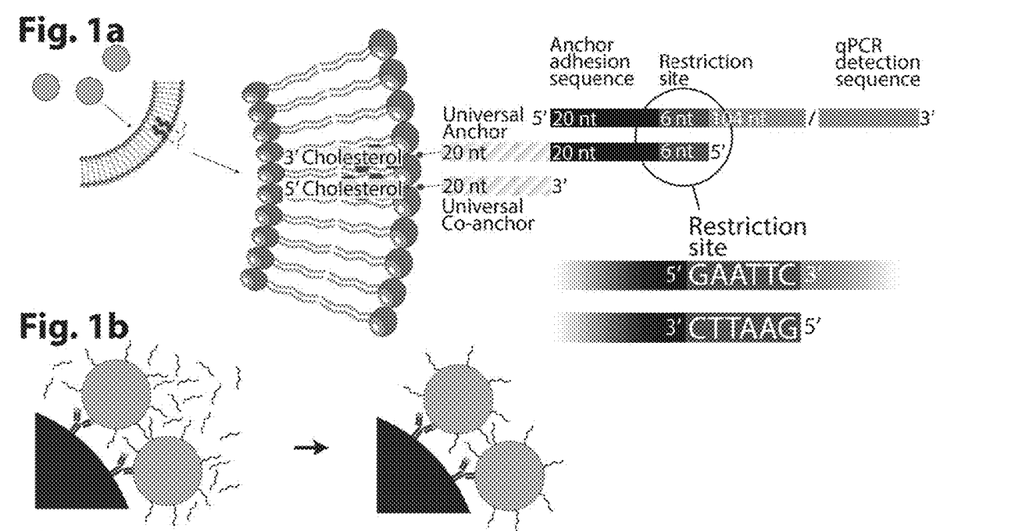
FIGS. 1a-1e: Workflow for ultrasensitive detection of lipid bilayer particles displaying specific surface antigens. a) Label particles with cholesterol-tagged 46 nt oligonucleotide (universal anchor), cholesterol-tagged 20 nt complementary oligonucleotide (co-anchor), and 130 nt oligonucleotide (detection oligo); b) capture ssDNA-labeled lipid bilayer particles on beads labeled with an antigen-binding moiety and wash to remove unbound ssDNA; c) cleave DNA from lipid bilayer particles using EcoR1 restriction enzyme; d) separate bead-bound lipid bilayer particles for downstream analysis and free detection oligo for quantification; e) qPCR using primers specific to detection oligo to obtain $C_T$ which corresponds to the number of lipid bilayer particles displaying the specific surface antigen.

We overcome the sensitivity limitation of current methods by labeling lipid bilayer particles ex vivo or in vitro with a single-stranded DNA oligonucleotide that can be quantified with extremely high sensitivity using qPCR. The label has three components: an anchor, a co-anchor, and a detection sequence that also contains a restriction site (FIGS. 1a-e). The anchor is modified with a 3' or 5' cholesterol or other bilayer embedding lipid molecule, and the co-anchor is modified with a 5' or 3' cholesterol or other bilayer embedding lipid molecule, both of which self-embed into the lipid bilayer membrane of lipid bilayer particles. Because the co-anchor is complementary to a portion of the anchor, these sequences hybridize via complementary base pairing, which prevents the anchor from dissociating from the membrane [5,6]. A second portion of the anchor, distal from the particle, hybridizes to a complementary portion of detection sequence, typically proximate to the particle. Hybridization of the detection and anchor oligos forms a double-stranded restriction site recognized by a restriction enzyme, such as an EcoR1 restriction site (FIG. 1a). In an embodiment the co-anchor oligo is 20 nt, the anchor oligo is 46 nt (20+20+6), and the detection oligo is 200 nt (20+6+174), or 130 nt (20+6+104); see FIGS. 1a-e.

The end-result of this labeling is a (e.g. 174 or 104 nt) ssDNA oligo tail tethered to the membrane of all lipid bilayer particles in a sample. This tail is engineered to be highly dissimilar to endogenous human DNA, thus enabling highly specific amplification of this sequence in a background of endogenous genetic material. Of note, this sequence can be of any length $\geq 60$ nt such that it can be captured by a complementary oligonucleotide or that detectable PCR amplicons can be produced. Specific PCR primers are designed to match this sequence.

Each lipid bilayer particle is stochastically labeled with many copies of the detection sequence, imparting exceptional sensitivity to our method, by saturating the particle solution with oligos. The ratio of oligo:particle can be adjusted to enhance the proportion of oligos that self-embed vs. wash away and thus increase the number of embedded oligos per particle. By amplifying this specific sequence, we can quantify the number of lipid bilayer particles with high sensitivity and dynamic range. Sensitivity and dynamic range can be tuned by adjusting the mean number of ssDNA labels per particle.

Figures 2A, 2B:
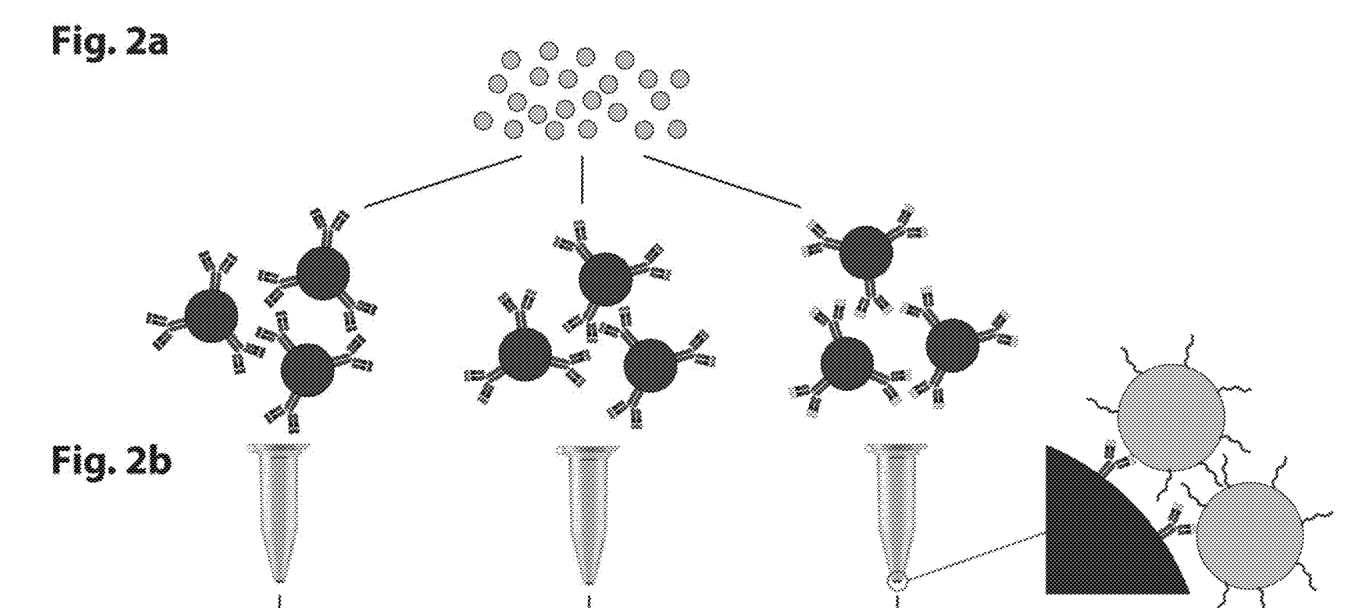
FIGS. 2a-2c: Multiplexing to detect multiple surface markers on lipid bilayer particles. a) oligo-labeled lipid bilayer particles are incubated with beads functionalized with different capture moieties; b) each tube or well contains lipid bilayer particles captured on beads via specific, distinct antigens; c) qPCR is performed in parallel for lipid bilayer particles captured via each moiety, thus producing a quantitative measure of the number of lipid bilayer particles displaying each antigen.
Figure 2C:
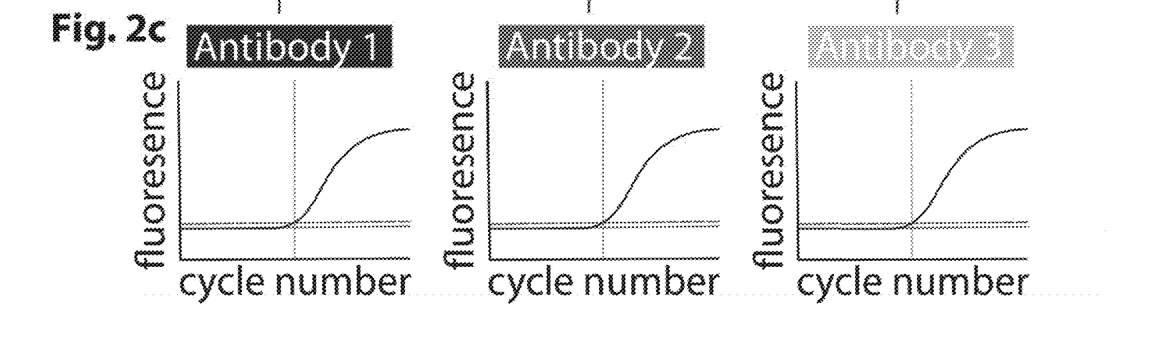

In combination with capture, our method enables the sensitive detection and enumeration of lipid bilayer particles displaying specific antigens. In this embodiment a solution containing lipid bilayer particles isolated using established isolation techniques is split among multiple vials, each containing paramagnetic beads functionalized with one or more specific antibodies (FIGS. 2a-c). Following a sufficient incubation, particles that do not display the antigens of interest are washed away. The quantity of ssDNA-labeled particles bound to beads via moieties that bind a specific antigen is then determined using qPCR, where the threshold cycle (cycle at which the signal produced by the intercalating dye exceeds a threshold) is directly correlated with the initial number of oligonucleotides present. This method thus produces a readout of the absolute quantity of lipid bilayer particles captured by each moiety.

Figure 3:
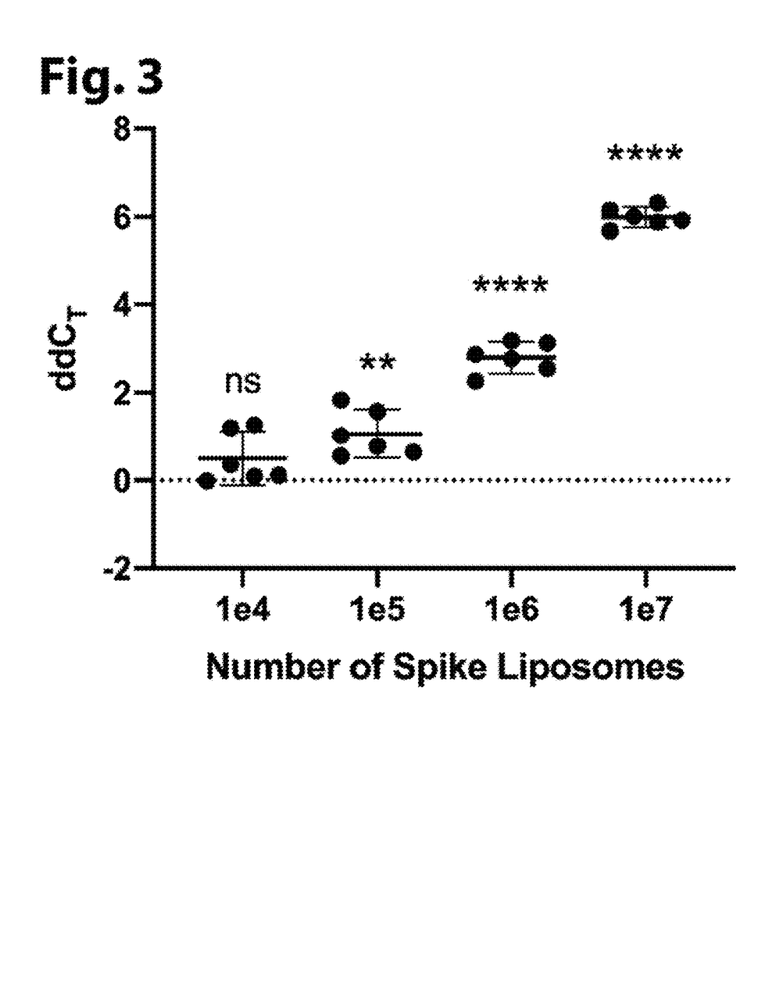
FIG. 3: Dilution curve of synthetic liposomes displaying spike protein captured on beads functionalized with biotinylated human ACE2. Signal from each sample containing spike-labeled liposomes was compared to the signal from a sample containing 1e7 unlabeled liposomes and to the signal from the PBS (no liposome) control. ns: not significant, : $p<0.01$, **: $p<0.0001$; error bars: standard deviation, n=6.

We quantified synthetic liposomes labeled with spike antigen (FIG. 3). We tagged 1e4, 1e5, 1e6, or 1e7 such liposomes suspended in 10 µl 0.2% BSA in PBS with 1 µl oligo (1e-12 mols=6.22e11 oligos). In parallel, 1 µl of oligo was added to PBS (no liposomes) and an equal number of liposomes without spike antigen, all of which were processed alongside the spike liposome samples. Liposomes were captured on beads functionalized with biotinylated human ACE2, then the beads were washed to remove free oligo and subjected to qPCR using primers specific to the synthetic oligo sequence. Signal from each sample containing spike-labeled liposomes was compared to the signal from a sample containing 1e7 unlabeled liposomes and to the signal from the PBS (no liposome) control.

Figure 4:
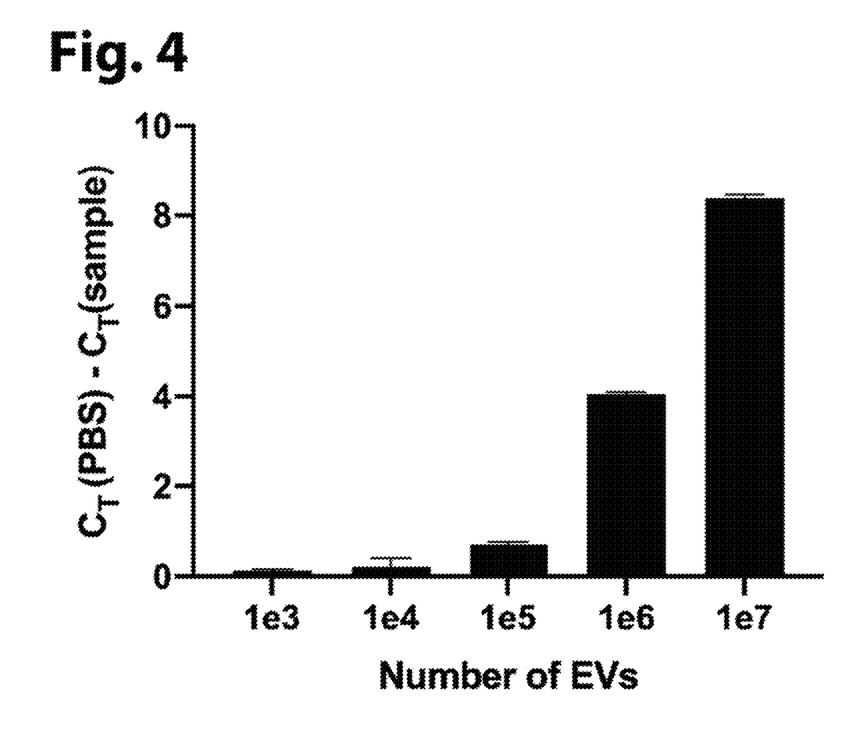
FIG. 4: Dilution curve of EVs derived from A549 cell culture supernatant captured on beads functionalized with biotinylated antibody against carbonic anhydrase 12, expression of which is upregulated in lung cancer. Error bars: standard deviation, n=3.

We quantified A549-derived EVs displaying a tumor-associated antigen (FIG. 4). We tagged 1e3, 1e4, 1e5, 1e6, or 1e7 EVs suspended in 10 µl 0.2% BSA in PBS with 1 µl oligo (1e-12 mols=6.22e11 oligos). In parallel, 1 µl of oligo was added to PBS (no EVs), which was processed alongside the EV samples. EVs were captured on beads functionalized with biotinylated antibody against carbonic anhydrase 12 (CA12), then the beads were washed to remove free oligo and subjected to qPCR using primers specific to the synthetic oligo sequence. Signal from each sample containing EVs was compared to the signal from the PBS (no EV) control.

Figure 5:
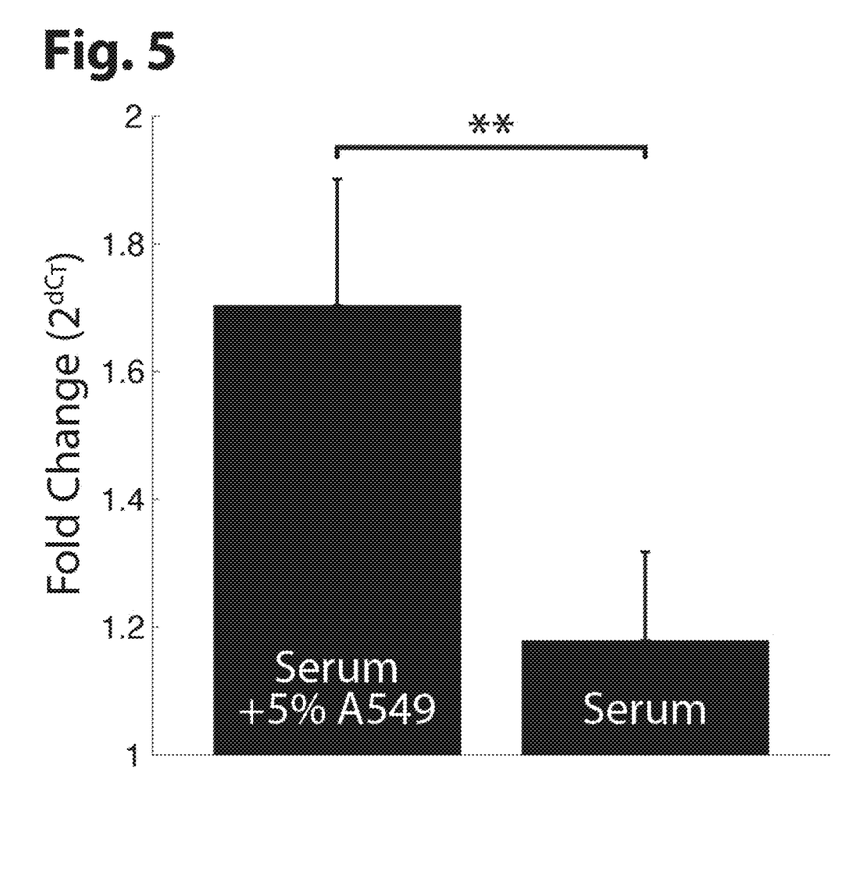
FIG. 5: Fold-change in signal due to EVs binding to CEACAM1-functionalized beads. Serum spiked with A549 EVs at a 1:20 ratio resulted in a fold-change in signal of 1.7×, significantly greater than the fold-change resulting from nonspecific binding of serum EVs of 1.18×, relative to the no-EV control ($p<0.01$, Student's t-test). Error bars: 95% confidence interval.
Figure 6A:
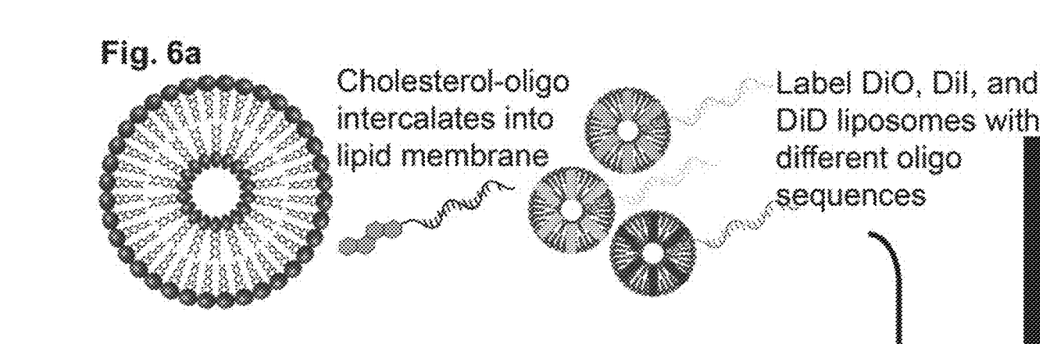
FIGS. 6a-6c: DNA-directed patterning of fluorescent liposomes. a) Fluorescent or plain liposomes can be tagged with single-stranded oligonucleotides based on the intercalation of a conjugated cholesterol molecule in the lipid bilayer; b) Photolithography-based DNA-directed patterning, in which photoresist is spin-coated onto aldehyde-coated slides, patterned with DV light through a photomask, and stripped following reductive amination of aldehyde groups with amine-terminated single-stranded oligonucleotides; c) Hybridization of oligo tags on the liposomes with complementary oligos patterned onto glass slides yields intricate and high-resolution patterns. Scale bar=500 μm.
Figure 6B:
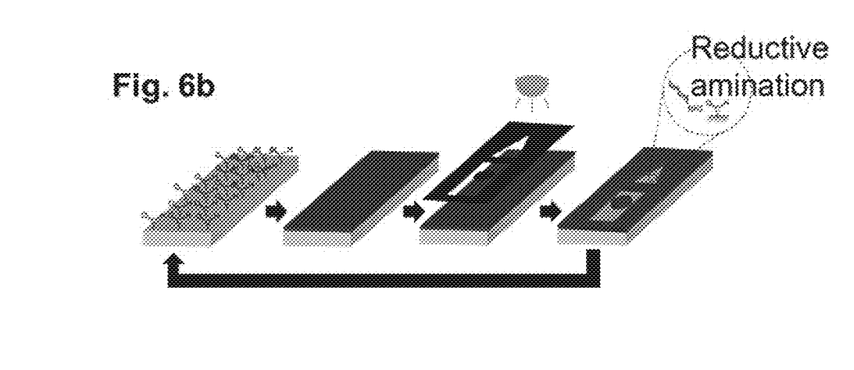
Figure 6C:
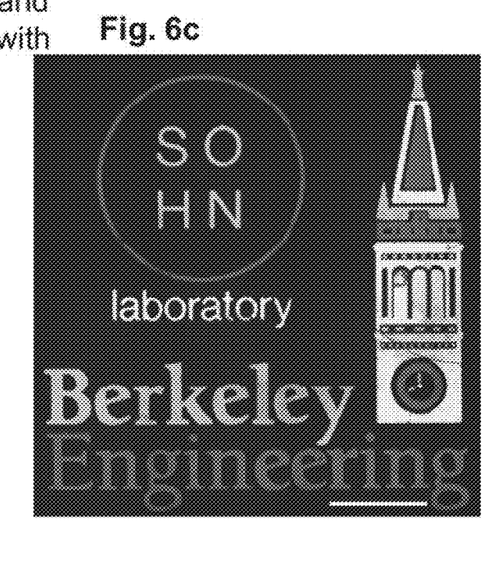
Figure 7A:
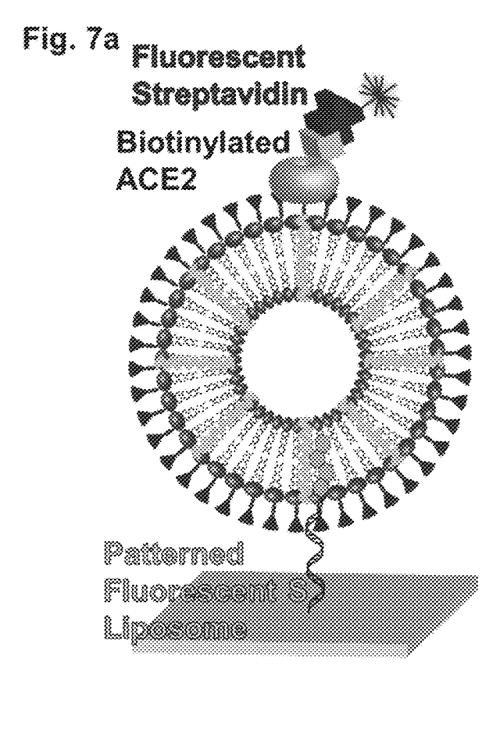
FIGS. 7a-7b: DNA-directed patterning to immobilize liposomes to test ACE2 binding. a) Schematic representation of DNA-instructed immobilization of fluorescent liposome displaying Spike protein, which binds with a biotinylated ACE2, which is detected using a Cy5-conjugated streptavidin. b) Microscopy image of fluorescent spike liposomes and biotinylated ACE2/Cy5-Streptavidin. Scale bar=100 μm.
Figure 7B:
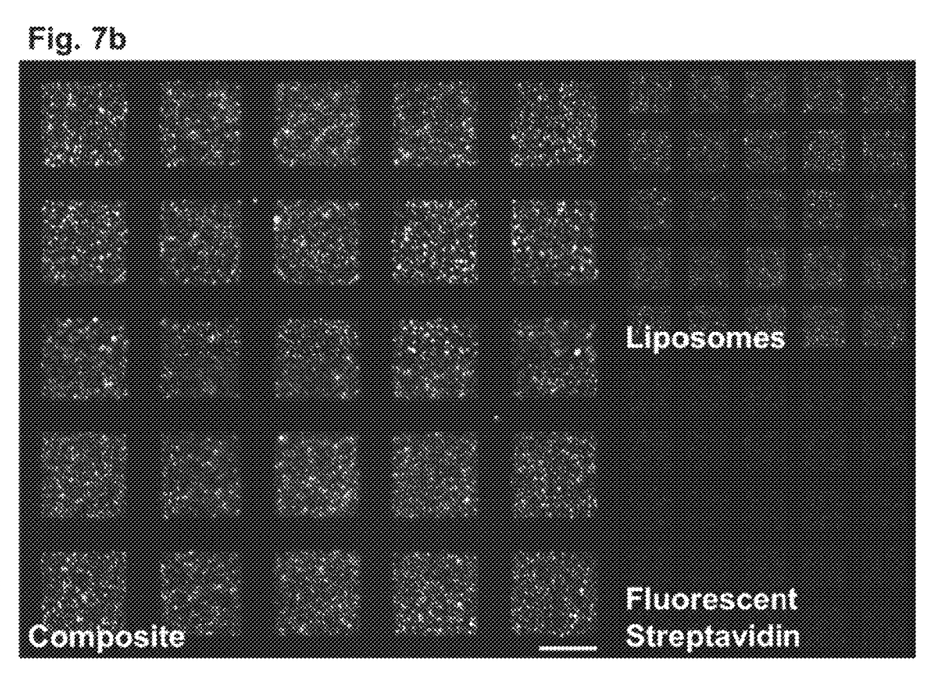

To further demonstrate the utility of this concept in a human biofluid, we quantified cell-culture-derived EVs spiked into healthy human donor serum. Briefly, 8 mL healthy donor serum was centrifuged for 15 min at 3000 g. 7.6 mL of clarified supernatant was recovered and split into two tubes with equal volume. Approximately 2e9 EVs isolated from A549 clarified cell culture supernatant in 200 µL buffer was spiked into one tube containing 3.8 mL clarified serum. In parallel, 200 µL buffer was added to the other tube containing 3.8 mL clarified serum. EVs were then isolated from both samples, and the buffer in which isolated EVs were recovered was exchanged for PBS and EVs were concentrated to 70 µL using ultrafiltration. EVs in PBS were then labeled with 1 µl oligo (1e-10 mols=6.22e13 oligos). Approximately 600,000 total EVs were captured on 3e5 beads functionalized with anti-CEACAM1 antibody, a marker known to be displayed on A549-derived EVs and absent on most normal-cell-derived EVs. Beads were then washed to remove free oligo and subjected to qPCR using primers specific to the synthetic oligo sequence. Signal for spiked serum and serum were compared to one another, normalized to the signal produced by a negative control consisting of all reaction components except oligo (FIG. 5). We further demonstrate our ability to immobilize liposomes for imaging or to characterize surface marker presentation (FIGS. 6a-b, 7a-b). Briefly, liposomes were tagged with ssDNA-cholesterol. Complementary ssDNA patterned on the surface enables hybridization and immobilization, after which biotinylated ACE2 can be added and detected by fluorescent streptavidin.

Figure 1C:
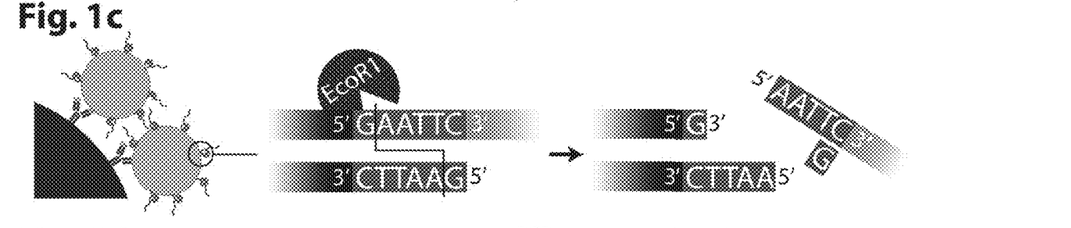
Figure 1D:
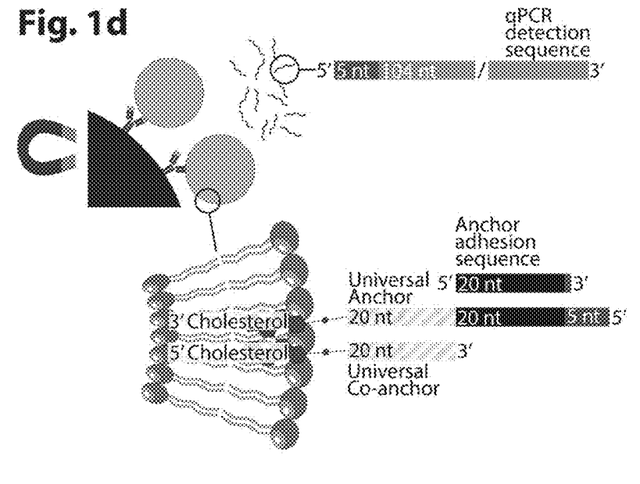
Figure 1E:
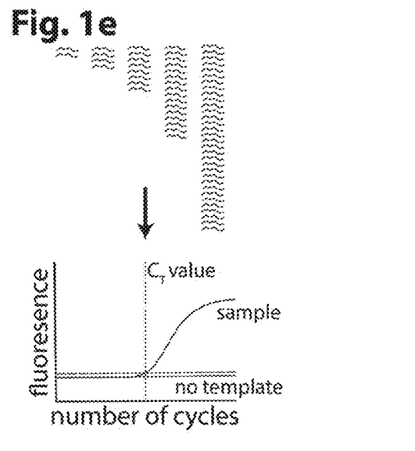

We can conduct our assay in a nondestructive fashion that allows recovery of all lipid bilayer particles in a sample. By including a restriction site in the region of the anchor complementary to the detection sequence (FIG. 1a), and following capture and washing of labeled particles (FIG. 1b), the anchor sequence can be cleaved with a corresponding restriction enzyme (FIG. 1c). This releases the free detection oligo into solution (FIG. 1d), which can then be separated easily from the bead-bound particles (FIG. 1e). PCR can then be conducted on the detection oligo, the concentration of which will be directly correlated with the quantity of particles captured by each antigen-binding moiety. Further downstream assays, such as RNA sequencing, can then be separately conducted on the particles.

Our methods enable determination of the number of RNA sequences per lipid bilayer particle displaying a particular surface antigen. At present, there is no other technologically feasible method to quantify the number of lipid bilayer particles displaying a specific surface antigen AND assay that same lipid bilayer particle population using RNA sequencing.

CITATIONS

[1] Reátegui E, Vos K E, Lai C P, Zeinali M, Atai N A, Aldikacti B, et al. Engineered nanointerfaces for microfluidic isolation and molecular profiling of tumor-specific extracellular vesicles. Nature Communications. Springer US; 2018 Jan. 5; 9(1):1-11.

[2] Ko J, Bhagwat N, Yee S S, Ortiz N, Sahmoud A, Black T, et al. Combining Machine Learning and Nanofluidic Technology To Diagnose Pancreatic Cancer Using Exosomes. ACS Nano. 2017 Oct. 17; acsnano.7b05503-12.

[3] Wan Y, et al. Enrichment of extracellular vesicles with lipid nanoprobe functionalized nanostructured silica. Lab on a Chip. Royal Society of Chemistry; 2019; 12:5-10.

[4] Chevillet J R, Kang Q, Ruf I K, Briggs H A, Vojtech L N, Hughes S M, et al. Quantitative and stoichiometric analysis of the microRNA content of exosomes. Proceedings of the National Academy of Sciences. 2014 Oct. 14; 111(41):14888-93.

[5] Weber R J, Liang S I, Selden N S, Desai T A, Gartner Z J. Efficient targeting of fatty-acid modified oligonucleotides to live cell membranes through stepwise assembly. Biomacromolecules. 2014 Dec. 8; 15(12): 4621-4626.

[6] Scheideler, O. J. et al. Recapitulating complex biological signaling environments using a multiplexed, DNA-patterning approach. Sci Adv 6, eaay5696 (2020).

The invention claimed is:

1. A method to quantify lipid bilayer particles displaying specific surface antigens, comprising:
    (a) labeling the particles with single-stranded DNAs (ssDNAs) each end-labeled with a membrane self-embedding lipid;
    (b) specifically capturing different subpopulations of the particles by specific antigen binding or complementary oligonucleotide hybridization;
    (c) employing a restriction enzyme to release the ssDNA label after the capture; and
    (d) using quantitative polymerase chain reaction (qPCR) quantification of the ssDNA to yield a quantitative readout that is directly correlated with the number of particles captured;
    wherein the labeling step comprises combining the particles with:
        i. an anchor oligo comprising: lipid-anchor sequence-adhesion sequence;
        ii. a co-anchor oligo comprising: lipid-anchor sequence'; and
        iii. a detection oligo comprising: adhesion sequence'-detection sequence;
    wherein the anchor oligo and at least one of the co-anchor oligo and detection oligo comprise complementary restriction sequences;
    wherein the ' indicates reverse complement, and the anchor is in opposite orientation from the co-anchor and detection oligos, such that:
    the lipids self-embed into the lipid bilayer membrane of the particles and anchor sequences hybridize via complementary base pairing, preventing the anchor oligo from dissociating from the membrane; the adhesion sequences hybridize, capturing the detection oligo onto the particles; and the restriction sequences hybridize, forming a double-stranded restriction site.

2. The method of claim 1, wherein the anchor oligo and detection oligo comprise the complementary restriction sequences.

3. The method of claim 1, wherein the anchor oligo and co-anchor oligo comprise the complementary restriction sequences.

4. The method of claim 1, wherein:
    the anchor oligo comprises: lipid-anchor sequence-adhesion sequence-restriction sequence; and
    the detection oligo comprises: adhesion sequence'-restriction sequence'-detection sequence.

5. The method of claim 1, wherein:
    the anchor oligo comprises: lipid-anchor sequence-restriction sequence-adhesion sequence; and
    the co-anchor oligo comprises: lipid-anchor sequence'-restriction sequence'.

6. The method of claim 1, wherein:
    the anchor oligo comprises: from 3' to 5': lipid-anchor sequence-adhesion sequence;
    the co-anchor oligo comprises: from 5' to 3': lipid-anchor sequence'; and
    the detection oligo comprises: from 5' to 3': adhesion sequence'-detection sequence.

7. The method of claim 1, wherein:
    the anchor oligo comprises: from 5' to 3': lipid-anchor sequence-adhesion sequence;
    the co-anchor oligo comprises: from 3' to 5': lipid-anchor sequence'; and
    the detection oligo comprises: from 3' to 5': adhesion sequence'-detection sequence.

8. The method of claim 1, wherein the anchor sequences are ≥10 nt, the adhesion sequences are ≥10 nt, the restriction sequences are 4-12 nt, and the detection sequence is ≥60 nt.

9. The method of claim 1, wherein the anchor sequences are 10-300 nt, the adhesion sequences are 10-300 nt, the restriction sequences are 3-12 nt, and the detection sequence is 20-2000 nt.

10. The method of claim 1, wherein the anchor sequences are 10-100 nt, the adhesion sequences are 10-100 nt, the restriction sequences are 4-12 nt, and the detection sequence is 20-500 nt.

11. The method of claim 1, wherein the anchor sequences are 10-30 nt, the adhesion sequences are 10-30 nt, the restriction sequences are 4-8 nt, and the detection sequence is 20-100 nt.

12. The method of claim 1, wherein the lipid is a steroid, lignoceric acid, dialkylphosphoglycerol, or a fatty acid amide.

13. The method of claim 1, wherein the particles are isolated from a human or animal bodily fluid, a cell culture medium, a medium containing bacteria, or are synthesized.

14. The method of claim 1, wherein the method quantifies a total number of particles and/or the quantities of different subpopulations of particles in a sample.

15. The method of claim 1, wherein the capturing step comprises contacting the particles with beads or surfaces functionalized with either a complementary oligonucleotide or a moiety that recognizes and specifically binds a specific antigen under conditions wherein particles displaying the antigen are retained on the beads or surfaces, and particles not displaying the antigen are washed away.

16. The method of claim 1, in multiplex format, wherein the capturing step comprises contacting subsets of the particles in separate containers, each with beads or surfaces functionalized with a moiety that recognizes a unique, specific antigen, under conditions wherein particles displaying the antigen are retained on the beads or surfaces, and particles not displaying the antigen are washed away.

17. The method of claim 1, wherein the lipid bilayer particles are extracellular vesicles (EVs).

18. The method of claim 1, wherein the lipid bilayer particles are enveloped viruses.

19. The method of claim 1, wherein the lipid bilayer particles are outer membrane vesicles.

20. The method of claim 1, wherein the lipid bilayer particles are liposomes.

* * * * *